United States Patent [19]

Carr et al.

[11] Patent Number: 4,868,194

[45] Date of Patent: Sep. 19, 1989

[54] IMIDAZOLE ANTIARRHYTHMICS

[75] Inventors: Albert A. Carr; John E. Koerner; Richard C. Dage; Tung Li; David A. Hay, all of Cincinnati, Ohio

[73] Assignee: Merrell Dow Pharmaceuticals Inc., Cincinnati, Ohio

[21] Appl. No.: 248,768

[22] Filed: Sep. 23, 1988

[51] Int. Cl.$^4$ ............... A61K 31/445; C07D 211/68; C07D 401/00

[52] U.S. Cl. .................................... 514/318; 546/194; 546/210; 546/197; 514/326; 514/321

[58] Field of Search ............... 546/194, 210, 197; 514/318, 326, 321

[56] References Cited

U.S. PATENT DOCUMENTS 4,791,121 12/1988 Kudzma et al. ............... 546/194

FOREIGN PATENT DOCUMENTS 0235752 9/1987 European Pat. Off. ............ 546/194

OTHER PUBLICATIONS

Selective Class III Antiarrhythmic Drug Candidates; Rationale and Serendipity in Design and Development of Different Structural Classes, William Lumma et al., presented at 21st National Medicinal Chemistry Symposium on Jun. 19-23, 1988 in Minneapolis, Minnesota.

Primary Examiner—Mary C. Lee
Assistant Examiner—Robert C. Whittenbaugh
Attorney, Agent, or Firm—J. Michael Dixon

[57] ABSTRACT

The present invention is directed to a new class of piperidinyl imidazole antiarrhythmic agents and to methods for treating arrhythmias.

28 Claims, No Drawings

IMIDAZOLE ANTIARRHYTHMICS

The present invention is directed to a class of piperidinyl imidazole antiarrhythmics. Another aspect of the invention is directed to a method for treating cardiac arrhythmias. A further aspect is directed to pharmaceutical compositions useful for treating cardiac arrhythmias. A final aspect is directed to an intermediate used in their production.

In accordance with the present invention, a new class of piperidinyl imidazole antiarrhythmics have been discovered which can be described by the following general formula:

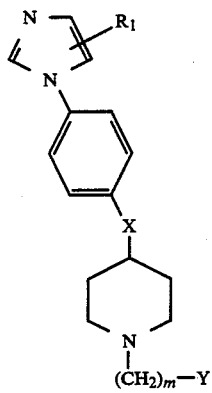

wherein X is represented by CO or CHOH; m is an integer from 1 to 5; $R_1$ is represented by hydrogen or a $C_{1-4}$ alkyl and Y is represented by one of the following aryl substituents:

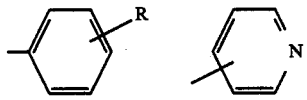

in which R is represented by a $C_{1-4}$ alkyl, $C_{1-4}$ alkoxy, halogen and hydrogen, or R is a divalent substituent and is represented by a 3,4-methylenedioxy or a 3,4-ethylenedioxy group; or a pharmaceutically acceptable acid addition salt thereof.

As used in this application:

(a) the term "halogen" refers to a fluorine, chlorine, or bromine atom;

(b) the term "alkyl" refers to a branched or straight chained alkyl group containing from 1–4 carbon atoms, such as methyl, ethyl, n-propyl, isopropyl, n-butyl and isobutyl;

(c) the term "alkoxy" refers to a straight or branched alkoxy group containing from 1–4 carbon atoms, such as methoxy, ethoxy, n-propoxy, isopropoxy, n-butoxy and isobutoxy;

(d) the term "carbonyl" refers to a substituent having the following structure:

the term "hydroxymethyl group" refers to the following substituent, —CHOH—;

(f) the terms "3,4-methylenedioxy or 3,4-ethylenedioxy" refers to the following substituent:

wherein n equals 1 or 2;

(g) the term "piperidinyl" refer to the following substituent:

(h) the terms "pyridinyl" and "pyridyl" refer to the following substituent and,

(i) the term "imidazolyl" refers to the following substituent.

The expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid and sulfonic acids such as methane sulfonic acid and 2-hydroxy-ethane sulfonic acid. Either the mono- or di-acid salts can be formed, and such salts can exist in either a hydrated or substantially anhydrous form. In general, the acid addition salts of these compounds are soluble in water and various hydrophilic organic solvents and which in comparison to their free base forms, generally demonstrate higher melting points.

Some of the compounds of Formula I exist as optical isomers. Any reference in this application to one of the compounds represented by Formula I is meant to encompass either a specific optical isomer or a mixture of optical isomers. The specific optical isomers can be separated and recovered by techniques known in the art such as chromatography on chiral stationary phases or resolution via chiral salt formation and subsequent separation by selective crystallization.

In the compounds of Formula I, the imidazole substituent is bonded to the 4-position of the indicated phenyl ring. When $R_1$ is represented by a $C_{1-4}$ alkyl, then that substituent can attach at any of positions 2, 4, or 5 of the imidazole ring. The imidazole ring is limited to substitution with a single alkyl moiety.

In those compounds of Formula I, wherein the aryl substituent Y is represented by a pyridine group, the pyridine ring may be bonded to the indicated alkylene bridging group at any of positions 2, 3, or 4 of the pyridine ring. The pyridine ring should remain unsubstituted.

In those compounds of Formula I, wherein the aryl substituent Y is represented by a phenyl ring and R is represented by a monovalent substituent, there can be up to 3 such substituents occurring on the indicated phenyl ring. These substituents can be located at any of positions 2–6 of the indicated phenyl ring. These substituents can be the same or can differ from one another. When R is represented by a divalent substituent (i.e. 3,4-methylene- or ethylene-dioxy), then the indicated phenyl ring is not substituted with any other substituents and the divalent substitution attaches at the 3 and 4 positions of the phenyl ring.

Representative examples of compounds encompassed by Formula I include:

(1) [4-(1H-imidazol-1-yl)phenyl][1-(2-phenylethyl)-4-piperidinyl]methanone;
(2) α-[4-(1H-imidazol-1-yl)phenyl]-1-(2-phenylethyl-4-piperidinemethanol;
(3) [4-(1H-imidazol-1-yl)phenyl][1-[2-(3,4-dimethoxyphenyl)ethyl]-4-piperidinyl]methanone;
(4) α-[4-(1H-imidazol-1-yl)phenyl]-1-[2-(3,4-dimethoxyphenyl)ethyl]-4-piperidinemethanol;
(5) [4-(1H-imidazol-1-yl)phenyl][1-(4-pyridylmethyl)-4-piperidinyl]methanone;
(6) α-[4-(1H-imidazol-1-yl)phenyl]-1-(4-pyridylmethyl)-4-piperidinemethanol;

The compounds of Formula I can be synthesized using techniques which are analogously known in the art. One method of synthesizing those compounds wherein X is represented by a carbonyl group (CO) is the following reaction scheme.

Initially an N-alkylation should be conducted between an aralkyl halide of Formula II and a piperidoyl derivative of Formula III as described below:

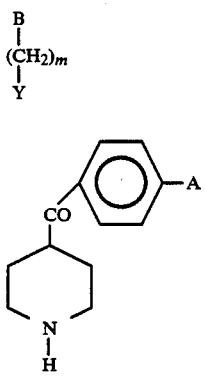

Formula II

Formula III in Formula II, Y and m are as defined in Formula I, and B is a halogen atom, preferably bromine. In Formula III, A is a halogen atom, preferably fluorine. The compounds of Formula II and III as well as methods for their production are known in the art.

This reaction produces an aryl piperidoyl intermediate as described by Formula IV:

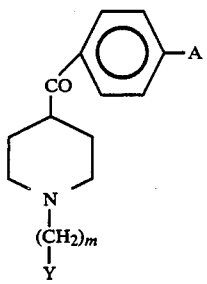

Formula IV wherein Y, m, and A are as defined above.

The aralkyl halide of Formula II which is utilized should be structurally analogous to its counterpart in the piperidinyl imidazole of Formula I since all of its substituents will be retained in the final product (with the exception of the halogen atom represented by B). The piperidoyl derivative of Formula III should not be substituted with any functional groups, with the exception of the para-halogen appearing on the indicated phenyl ring.

For example if the desired piperidinyl imidazole derivative of Formula I is [4-(1H-imidazol-1-yl)phenyl][1-(2-phenylethyl)-4-piperidinyl]methanone; then 4-fluorophenyl-4-piperidinyl methanone is reacted with 1-halo-2-phenylethane thereby producing the intermediate of Formula IV, 4-fluorophenyl[1-(2-phenylethyl)-4-piperidinyl]methanone.

The N-alkylation reaction can be conducted utilizing techniques known in the art. Typically approximately equimolar quantities of the aralkyl halide and the piperidoyl derivative will be contacted with a weak base such as potassium bicarbonate. A moderate excess of either of the starting materials is not deleterious to the reaction. The base is typically present in the reaction medium in a quantity of from about 1 mole to about 4 moles for every mole of piperidoyl reactant utilized. The reaction is also typically conducted in the presence of a catalytic amount of potassium iodide. The reactants are typically stirred together for a period of time ranging from about 2 hours to about 72 hours at a temperature range of about 20° C. to about 110° C. The reaction is also typically conducted in an organic solvent such as, for example, toluene, acetonitrile, or dimethylformamide.

The aryl piperidoyl intermediate can be recovered and separated utilizing a variety of techniques known in the art. For example, the aryl piperidoyl intermediate will precipitate from solution upon the formation of its hydrochloride acid addition salt, thus allowing its recovery by filtration. This precipitate can be formed utilizing techniques known in the art, such as the addition of hydrogen chloride to the reaction zone. Alternatively, water can be added to the reaction zone of the original mixture and the intermediate can be recovered by conventional extraction techniques.

The intermediate can also be purified by several techniques known in the art. When the intermediate is recovered by precipitation of the hydrochloride acid addition salt, the original reaction medium is typically filtered through suitable chromatographic separation material, such as silica gel, prior to the formation of the hydrochloride precipitate. The resulting precipitate is typically subjected to recrystallization in a solvent system such as methanol/butanone or 2-propanol. When the intermediate is recovered by extraction, the resulting extract is typically filtered through silica gel or subjected to other chromatographic purification techniques. After concentration of the eluent, the resulting concentrated residue is typically recrystallized from a solvent system such as ethyl acetate, ethyl acetate/hexane, cyclohexane, or the like.

The piperidinyl imidazole derivative of Formula I can then be produced by conducting a N-arylation reaction between an imidazole derivative as described by Formula V below, in which $R_1$ is represented by hydrogen or a $C_{1-4}$ alkyl, and the aryl piperidoyl intermediate of Formula IV:

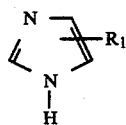

Formula V

The particular imidazole derivative which is utilized should be structurally analogous to its counterpart in the piperidinyl imidazole of Formula I since all of its nonreactive substituents will be retained in the final product. For example, if the desired piperidinyl imidazole of Formula I is [4-(1H-imidazol-1-yl)phenyl][1-(2-phenylethyl)-4-piperidinyl]methanone, then 4-fluorophenyl[1-(2-phenyl-ethyl)-4-piperidinyl]methanone should be reacted with imidazole.

The N-arylation can be conducted utilizing techniques which are analogously known in the art. Generally approximately equimolar quantities of the aryl piperidoyl intermediate of Formula IV and the imidazole derivative of Formula V are contacted in the presence of a weak base such as potassium carbonate. The base is typically present in the quantity of from about one mole to about two moles for every mole of the imidazole derivative present.

The reactants are typically stirred together at a temperature range of from about 20° C. to about 150° C., preferably 120°–150° C., for a period of time ranging from about 2 hours to about 72 hours, preferably 48–72 hours, under an inert atmosphere such as argon. The N-arylation is typically conducted in the presence of a solvent such as dimethyl sulfoxide, or N,N-dimethylformamide.

The piperidinyl imidazole of Formula I can be recovered and purified using techniques known in the art. For example, water can be added to the reaction medium which causes the precipitation of the piperidinyl imidazole of Formula I. The crude precipitate is then optionally recovered, dissolved in an organic solvent such as dichloromethane, washed with water, and the resulting organic layer is then dried and concentrated. The piperidinyl imidazole can then be purified by subjecting the resulting concentrate to flash chromatography on silica gel using an organic solvent such as acetone as the eluting agent. The resulting eluent is then concentrated and the residue is recrystallized from a solvent system such as 2-butanone/hexane or ethyl acetate. Other suitable solvent systems will be readily apparent to those skilled in the art.

An alternative preparation of the compounds of Formula I wherein X is a carbonyl group comprises initially attaching an amino protecting group on the piperidoyl derivative of Formula III described above. This can be done using techniques known in the art. Suitable amino protecting groups include a t-BOC substituent. Another suitable amino protecting group is a carbobenzoxy group. Each amino protecting group can be attached using techniques well known in the art.

The next step in the reaction scheme is to conduct an N-arylation reaction between the N-protected piperidoyl derivative of Formula III and the previously described imidazole derivative of Formula V. This yields a piperidinyl imidazole intermediate of Formula VI:

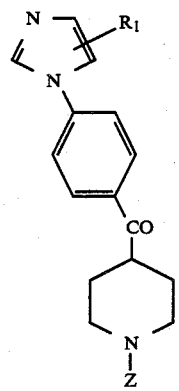

Formula VI wherein $R_1$ is as defined in Formula I and Z is an amino protecting group.

This intermediate is produced utilizing reaction conditions analogous to those previously described for the N-arylation reaction between the aryl piperidoyl intermediate of Formula IV and the imidazole derivative of Formula V. The intermediate of Formula VI can also be recovered and purified by techniques known in the art such as flash chromatography on silica gel, followed by recrystallization from a solvent such as cyclohexane.

The amino protecting group is then removed from the piperidinyl imidazole intermediate utilizing techniques known in the art such as contacting the intermediate with either a mineral acid or trifluroacetic acid. After basification, the resulting free base can be recovered and purified utilizing technniques known in the art, prior to its subsequent utilization in the synthesis.

The final step in the alternative reaction scheme is an N-alkylation reaction between the resulting deprotected piperidinyl imidazole intermediate of Formula VI in which Z is represented by hydrogen, and the previously described aralkyl halide of Formula II. This N-alkylation can be accomplished using reaction conditions analogous to that previously described for the N-alkylation between the compounds of Formula II and III. The compound of Formula I is then recovered and purified utilizing those same methods discussed above for the compounds of Formula I.

Those compounds of Formula I in which X is represented by CHOH, (i.e. a hydroxymethylene group), can be produced in the following manner. Initially, a piperidinyl imidazole of Formula I is produced that is structurally identical to the desired compound with the exception of X being represented by CO. This can be done using the techniques taught above. This compound is then reduced, thereby producing the desired compound of Formula I wherein X is represented by CHOH.

For example, α-[4-(1H-imidazol-1-yl)phenyl]-1-(2-phenylethyl-4-piperidinemethanol can be produced by reducing [4-(1H-imidazol-1-yl)phenyl][1-(2-phenylethyl)-4-piperidinyl]methanone.

Typically the reduction is accomplished by contacting the piperidinyl imidazole of Formula I in which X is represented by CO, with an alkali metal borohydride such as sodium or potassium borohydride. The borohydride reducing agent is present in the quantity of from about 0.5 moles to about 4 moles for every mole of piperidinyl imidazole present. The reduction is typically conducted at a temperature range of from about 0° C. to about 50° C., preferably from about 0° C. to room temperature, for a period of time ranging from about 1 hour to about 72 hours. The reaction is also typically conducted in an alcoholic solvent, such as methanol.

The resulting piperidinyl imidazole in which X is represented by CHOH, can be recovered and purified using a variety techniques known in the art. Typically the piperidinyl imidazole is purified by filtering the reaction medium through silica gel. The resulting filtrate is then concentrated in order to recover the piperidinyl imidazole. Prior to further purification the residue is dissolved in an organic solvent and washed with water, dried and reconcentrated. The hydroxymethyl containing piperidinyl imidazole can be further purified by subjecting the resulting concentrate to recrystallization in 2-butanone or tetrahydrofuran. If desired the recrystallization can be repeated to assure purity.

Alternatively, water can be added to the reaction medium and the resulting solution is then concentrated until a suspension is obtained. The resulting suspension is extracted with an organic solvent such as dichloromethane and dried. The resulting organic layers are filtered through a suitable chromatographic separation material, such as silica gel, utilizing an organic solvent such as acetone, as the eluting agent. The resulting eluent is concentrated and the concentrated residue is subjected to recrystallization in a suitable solvent such as 2-butanone or tetrahydrofuran.

The compounds of Formula I can be administered by a variety of routes. They are effective if administered either orally or parenterally (i.e., intravenously, intramuscularly, or subcutaneously).

The compounds of the present invention are useful as cardiac antiarrhythmic agents. They can be administered to a patient suffering from an arrhythmic episode in order to terminate the arrhythmic episode and return the myocardium to a normal sinus rhythm or the compound can be administered on a prophylactic basis in order to prevent the occurrence of arrhythmic episodes.

The compounds of Formula I increase the duration of the action potential of myocardial tissue producing an increase in the refractory period of that tissue. Thus, under the classification system of Vaughan Williams these compounds exhibit a Class III antiarrhythmic activity.

One method of demonstrating the antiarrhythmic activity of these compounds is the following test protocol. This protocol demonstrates what effect a compound has upon the action potential of isolated cardiac tissue, such as a Purkinje fiber from a dog heart or a papillary muscle from a guinea pig heart.

The heart of an anesthetized mongrel dog is surgically removed and the Purkinje fibers are dissected from either of the ventricles. Alternately, papillary muscles are removed from the right cardiac ventricle of a guinea pig. A Purkinje fiber or a papillary muscle is then placed in a tissue bath which is continuously perfused with modified Tyrode's solution[1].

[1] The modified Tyrode's solution has the following composition (in mmol): NaCl 127.0, KCl 5.4, $NaH_2PO_4$ 0.5, $MgCl_2$ 1.0, $NaHCO_3$ 23.8, $CaCl_2$ 1.8 and glucose 11.1. A gas mixture comprised of 95% $O_2$ and 5% $CO_2$ is bubbled through the solution while it is maintained within a pH range of from 7.3–7.4.

The electrophysiology of the cardiac tissue is monitored by conventional glass microelectrodes. One microelectrode is inserted into a cell in the cardiac muscle fiber and a ground electrode is positioned in the tissue bath. A conventional oscilloscope is utilized to visualize the action potential waveforms of the cardiac cell.

The cardiac muscle fiber is electrically stimulated at a frequency of 1 Hz through a pair of platinum plates placed in the tissue bath. This stimulation is continued for approximately 1 hour in order to allow the electrophysiological characteristics of the fiber to stabilize.

After approximately 1 hour, the fiber should be exhibiting a stable action potential as demonstrated by the waveform displayed on the oscilloscope. At this point, representative control action potentials are recorded and analyzed by a computer.

After establishing a control action potential, the test compound is introduced into the Modified Tyrode's solution in a quantity such that the test compound is present within the tissue bath in a range of from $10^{-8}$ to $10^{-5}$ moles/liter. After the effect of the test compound has reached a steady state, the action potential is again recorded and analyzed in the manner described above.

The compounds of the present invention having Class III antiarrhythmic properties are useful for treating a variety of arrhythmic conditions of the heart. Representative examples of arrhythmic conditions which are amenable to treatment with the compounds of the present invention include atrial tachycardia, atrial flutter, atrial fibrillation, and life threatening ventricular arrhythmias such as ventricular tachycardia, or ventricular fibrillation. These compounds will prevent recurrent episodes of the ventricular arrhythmias mentioned above.

The quantity of compound needed to either terminate an arrhythmic episode or prevent the occurrence of an arrhythmic episode (i.e., an antiarrhythmic quantity) will vary depending upon the route of administration, the patient, the severity of the patient's condition, the presence of other underlying disease states, and the particular compound utilized. However as a general guideline, if the compound is being administered orally, then it is preferably administered within a dosage range of from about 1.0 mg/kg of patient body weight/day to about 400.0 mg/kg of patient body weight/day. Likewise, if the compound is being administered parenterally then it is preferably administered within a dosage range of from about 0.1 mg/kg of patient body weight/day to about 120.0 mg/kg of patient body weight/day.

Repetitive daily administration of the compounds may be desired and will vary with the conditions outlined above for the quantity of compound utilized.

The patient's response to the compound can be monitored via an EKG or any other technique conventionally used in the art.

As used in this application:

(a) the term "patient" refers to a warm-blooded animal, such as for example rats, mice, dogs, cats, guinea pigs, and primates such as humans.

(b) the term "arrhythmia" refers to any variation from the normal rhythm of the heart beat.

(c) the phrase "antiarrhythmic amount" refers to the amount of a compound that is utilized in either preventing or alleviating an arrhythmia.

(d) the phrase "to treat an arrhythmia or treatment of an arrhythmia" refers to the capability of the compounds to either terminate an arrhythmic episode or lessen its severity as well the capability of the compounds to prevent the occurrence of an arrhythmic episode when administered prophylactically.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compounds of Formula I can be tableted with conventional tablet bases such as lactose, sucrose, and cornstarch in combination with binders, such as acacia, cornstarch, or gelatin, disintegrating agents such as potato starch or algenic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration, the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc. as are known in the art.

The following examples are presented in order to further illustrate the invention, but should not be construed as limiting the invention in any manner.

EXAMPLE I

The purpose of this example is to demonstrate one method for the preparation of an aryl piperidoyl intermediate as described by Formula IV.

A solution of 4-fluorophenyl-4-piperidinyl methanone (20.7 g, 99.7 mmol) and 1-bromo-2-phenyl-ethane (20.3 g, 110 mmol) in toluene (100 ml) was prepared, treated with potassium bicarbonate (40 g, 400 mmol) and potassium iodide (catalytic amount). The resulting mixture was then refluxed for 72 hours. Toluene (100 ml) was added, the resulting slurry filtered, and the filtrate was treated with hydrogen chloride in ether to afford a white solid. The solid was recrystallized from methanol/butanone to yield 4-fluorophenyl[1-(2-phenylethyl)-4-piperidinyl]methanone monohydrochloride (18.9 g, 55%) as white crystals: m.p. 256°–258° C.

EXAMPLE II

The purpose of this example is to demonstrate one method for the preparation of a piperidinyl imidazole as defined by Formula I.

A solution of 4-fluorophenyl[1-(2-phenylethyl)-4-piperidinyl]methanone (17.5 g, 56.2 mmol, prepared as in Example I) and imidazole (3.83 g, 56.3 mmol) was prepared in dimethylsulfoxide (90 ml), treated with potassium carbonate (8.7 g, 63 mmol), and stirred under argon at 120° C. for 48 hours. The cooled solution was poured into cold water (1 L), and the resulting slurry filtered to afford a white solid. The solid was dissolved in dichloromethane, washed twice with water, dried (MgSO$_4$), and evaporated to give a tan solid (18.8 g).

This solid was chromatographed on silica gel, eluting with acetone to afford the product as a white solid (9.9 g, 27 mmol, 49%). This was recrystallized from 2-butanone/hexane to yield [4-(1H-imidazol-1-yl)phenyl][1-(2-phenylethyl)-4-piperidinyl]methanone as a white, crystalline material (23%): m.p. 143°–144.5° C.

EXAMPLE III

The purpose of this example is to demonstrate one method for the preparation of piperidinyl imidazole as described by Formula I wherein X is represented by a hydroxymethylene group.

To a stirred solution of [4-(1H-imidazol-1-yl)phenyl][1-(2-phenylethyl)-4-piperidinyl]methanone (5.00 g, 13.9 mmol) in methanol (350 ml) at 0° C. was added sodium borohydride (600 mg, 15.9 mmol) in one portion. After stirring two hours, the solution was filtered through a pad of silica gel and then concentrated to an amber oil. The oil was dissolved in ethyl acetate, washed twice with water, once with brine, dried (MgSO$_4$), and evaporated to give a tan from 2-butanone to give α-[4-(1H-imidazol-1-yl)phenyl]-1-(2-phenylethyl-4-piperidinemethanol as a vanilla colored powder (1.6 g, 32%): m.p. 162°–163° C.

EXAMPLE IV

The purpose of this example is to demonstrate a method for producing an intermediate of Formula IV.

A solution of 4-fluorophenyl-4-piperidinyl methanone monohydrochloride (27.5 g, 113 mmol) and 1-bromo-2-(3',4'-dimethoxyphenyl)-ethane (27.3 g, 111 mmol) was prepared in N,N-dimethyl-formamide (400 ml), treated with potassium carbonate (30.0 g, 217 mmol) and potassium iodide (catalytic amount), and stirred under argon at 95° C. for 20 hours. The cooled solution was concentrated and poured into water. This aqueous suspension was extracted twice with ethyl acetate. The combined organic layers were dried (MgSO$_4$), filtered through a pad of silica gel, and treated with hydrogen chloride in ethyl acetate to afford a white solid. The solid was recrystallized from 2-propanol to yield (4-fluorophenyl)[1-[2-(3,4-dimethoxyphenyl)ethyl]-4-piperidinyl]methanone hydrochloride as white crystals (24.0 g, 53%): m.p. 200°–201° C.

EXAMPLE V

The purpose of this example is to demonstrate a method for producing an intermediate of Formula IV, where Y is represented by an pyridinyl alkyl group.

To a stirred solution of 4-fluorophenyl-4-piperidinyl methanone monohydrochloride (5.00 g, 20.5 mmol) and 4-picolyl chloride hydrochloride (3.36 g, 20.5 mmol) in water (20 ml) was added potassium carbonate (7.10 g, 51.4 mmol). Acetonitrile (200 ml) was added and the solution was refluxed for 20 hours. The cooled solution was filtered, concentrated, and the resulting oil was partitioned between water and dichloromethane. The layers were separated and the aqueous layer was extracted with dichloromethane. The combined organic layers were dried (MgSO$_4$), and filtered through a pad of silica gel (eluting with ethyl acetate). The eluent was concentrated and the resulting solid was recrystallized from 2-propanol to afford (4-fluorophenyl)[1-[2-(4-pyridinyl) methyl]-4-piperidinyl]methanone as a white powder (3.0 g, 49%): m.p. 139°–140° C.

EXAMPLE VI

The purpose of this example is to demonstrate a method for the production of a piperidinyl imidazole of Formula I.

A solution of (4-fluorophenyl)[1-[2-(3,4-dimethoxyphenyl)ethyl]-4-piperidinyl]methanone (15.7 g, 42.3 mmol) and imidazole (2.9 g, 42.6 mmol) was prepared in methyl sulfoxide (60 ml), treated with potassium carbonate (6.78 g, 49.1 mmol), and stirred under argon at 120° C. for 70 hours. The cooled solution was poured into water and extracted twice with ethyl acetate. The combined organic layers were washed twice with water, once with brine, dried (MgSO$_4$), and filtered through a pad of silica gel (eluting with acetone). The eluent as concentrated and the resulting solid was recrystallized from ethyl acetate to afford [4-(1H-imidazol-1-yl)phenyl][1-[2-(3,4-dimethoxyphenyl)ethyl]-4-piperidinyl]methanone as white crystals (4.1 g, 23%): m.p. 135°–136° C.

EXAMPLE VII

The purpose of this example is to demonstrate a method for producing a piperidinyl imidazole of Formula I in which X is represented by CO.

A solution of (4-flurophenyl)[1-[2-(4-pyridinyl)methyl]-4-piperidinyl]methanone (24.9 g, 83.5 mmol) and imidazole (5.70 g, 83.7 mmol) was prepared in methylsulfoxide (150 ml), treated with potassium carbonate (13.6 g, 98.6 mmol), and stirred under argon at 120° C. for 70 hours. The cooled solution was poured into water and extracted three times with dichloromethane. The combined organic layer were dried (MgSO$_4$), and concentrated. The resulting solid was chromatographed on silica gel (100×150 mm), eluting with acetone. The appropriate fractions were combined and concentrated to afford or solid which was recrystallized from ethyl acetate to yield [4-(1H-imidazol-1-yl)phenyl][1-(4-pyridylmethyl)-4-piperidinyl]methanone (19.5 g, 67%): m.p. 121°–122° C.

EXAMPLE VIII

The purpose of this example is to demonstrate a method for producing a piperidinyl imidazole of Formula I in which X is represented by CHOH.

To a stirred solution of [4-(1H-imidazol-1-yl)phenyl][1-[2-(3,4-dimethoxyphenyl)ethyl]-4-piperidinyl]methanone (5.90 g, 14.1 mmol) in methanol (100 ml) at 0° C. was added sodium borohydride (1.80 g, 47.6 g mmol) in three equal portions over a 24 hour period. Water was added and the solution was concentrated to a white suspension. This aqueous suspension was extracted twice with dichloromethane. The combined organic layers were dried (MgSO$_4$), and filtered through a pad of silica gel (eluting with acetone). The eluent was concentrated and the resulting solid was recrystallized from tetrahydrofuran to afford α-[4-(1H-imidazol-1-yl)phenyl]-1-[2-(3,4-dimethoxyphenyl)ethyl]-4-piperidine methanol (2.9 g, 49%): m.p. 59°–60° C.

EXAMPLE IX

The purpose of this example is to demonstrate a method for the preparation of piperidinyl imidazole of Formula I in which X is represented by CHOH.

To a stirred solution of [4-(1H-imidazol-1-yl)phenyl][1-(4-pyridylmethyl)-4-piperidinyl]methanone (5.70 g, 16.5 mmol) in methanol (100 ml) at 0° C. was added sodium borohydride (2.1 g, 56 mmol) in three equal portions over a 24 hour period. Water was added and the solution was concentrated to a white suspension. This aqueous suspension was extracted three times with dichloromethane. The combined organic layers were dried (MgSO$_4$), and filtered through a pad of silica gel (eluting with acetone). The eluent was concentrated and the resulting solid was recrystallized from tetrahydrofuran to afford the desired product, α-[4-(1H-imidazol-1-yl)phenyl]-1-(4-pyridylmethyl)-4-piperidine methanol (2.5 g, 43%): m.p. 174°–175° C.

What is claimed is:

1. A compound of the formula:

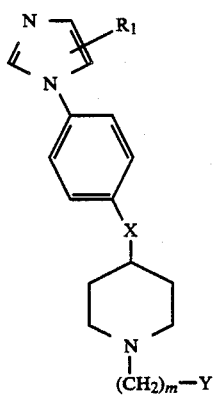

wherein X is CO or CHOH; m is an integer from 1 to 5; R$_1$ is hydrogen or a C$_{1-4}$ alkyl and Y is an aryl substituent of the formulae:

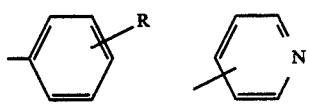

in which R is a monovalent substituent and is selected from the group consisting of a C$_{1-4}$ alkyl, C$_{1-4}$ alkoxy, halogen and hydrogen, or R is a divalent substituent and is a 3,4-methylenedioxy or a 3,4-ethylenedioxy group; or a pharmaceutically acceptable acid addition salt thereof.

2. A compound according to claim 1, wherein X is CO.

3. A compound according to claim 1, wherein X is CHOH.

4. A compound according to claim 2, wherein Y is

5. A compound according to claim 2, wherein Y is

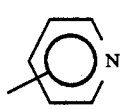

6. A compound according to claim 3, wherein Y is

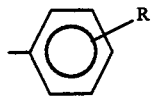

7. A compound according to claim 3, wherein Y is

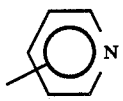

8. A method for the treatment of cardiac arrhythmias comprising administering to a patient in need thereof, an antiarrhythmic amount of a compound according to claim 1.

9. A pharmaceutical composition comprising a compound according to claim 1 present in an antiarrhthymic quantity in admixture with a pharmaceutically acceptable carrier.

10. A compound of the formula:

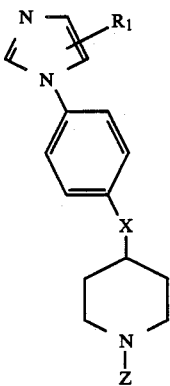

wherein $R_1$ is hydrogen or a $C_{1-4}$ alkyl, X is a carbonyl and Z is an amino protecting group wherein said amino protecting group is a 1,1-dimethyethloxycarbonyl substituent or a carbobenzoxy substituent.

11. A composition according to claim 1 wherein said compound is [4-(1H-imidazol-1-yl)penyl][1-(2-phenylethyl)-4-piperidinyl]methanone.

12. A compound according to claim 1 wherein said compound is α[4-(1H-imidazol-1-yl)phenyl]-1-(2-phenylethyl-4-piperidinemethanol.

13. A compound according to claim 1 wherein said compound is [4-(1H-imidazol-1-yl)phenyl][1-[2-(3,4-dimethoxyphenyl)ethyl]-4-piperidinyl]methanone.

14. A compound according to claim 1 wherein said compound is α-[4-(1H-imidazol-1-yl)phenyl]-1-[2-(3,4-dimethoxylphenyl)ethyl]-4-piperidinemethanol.

15. A compound according to claim 1 wherein said compound is [4-(1H-imidazol-1-yl)phenyl][1-(4-pyridylmethyl)-4-piperidinyl]methanone.

16. A compound according to claim 1 wherein said compound is α-[4-(1H-imidazol-1-yl)phenyl]-1-(4-pyridylmethyl)-4-piperidinemethanol.

17. A method according to claim 8 wherein said compound is [4-(1H-imidazol-1-yl)phenyl][1-(2-phenylethyl)-4-piperidinyl]methanone.

18. A method according to claim 8 wherein said compound is α-[4-(1H-imidazol-1-yl)phenyl]-1-(2-phenylethyl)-4-piperidinemethanol.

19. A method according to claim 8 wherein said compound is [4-(1H-imidazol-1-yl)phenyl][1-[2-(3,4-dimethoxyphenyl)ethyl]-4-piperidinyl]methanone.

20. A method according to claim 8 wherein said compound is α-[4-(1H-imidazol-1-yl)phenyl]-1-[2-(3,4-dimethoxyphenyl)ethyl]-4-piperidinemethanol.

21. A method according to claim 8 wherein said compound is [4-(1H-imidazol-1-yl)phenyl][1-(4-pyridylmethyl)-4-piperidinyl]methanone.

22. A method according to claim 8 wherein said compound is α-[4-(1H-imidazol-1-yl)phenyl]-1-(4-pyridylmethyl)-4-piperidinemethanol.

23. A composition according to claim wherein said compound is [4-(1H-imidazol-1-yl)phenyl][1-(2-phenylethyl)-4-piperidinyl]methanone.

24. A composition according to claim 9 wherein said compound is α-[4-(1H-imidazol-1-yl)phenyl]-1-(2phenylethyl-4-piperidinemethanol.

25. A composition according to claim 9 wherein said compound is [4-(1H-imidazol-1-yl)phenyl][1-[2-(3,4-dimethoxyphenyl)ethyl]-4-piperidinyl]methanone.

26. A composition according to claim 9 wherein said compound is α-[4-(1H-imidazol-1-yl)phenyl]-1-[2-(3,4-dimethoxyphenyl)ethyl]-4-piperidinemethanol.

27. A composition according to claim 9 wherein said compound is [4-(1H-imidazol-1-yl)phenyl][1-(4-pyridylmethyl)-4-piperidinyl]methanone.

28. A composition according to claim 9 wherein said compound is α-[4-(1H-imidazol-1-yl)phenyl]-1-(4-pyridylmethyl)-4-piperidinemethanol.

* * * * *